United States Patent
Bell (10) Patent No.: US 6,695,879 B2
(45) Date of Patent: Feb. 24, 2004

(54) CARDIOVASCULAR COMPONENTS FOR TRANSPLANTATION AND METHODS OF MAKING THEREOF

(75) Inventor: Eugene Bell, Boston, MA (US)

(73) Assignee: TEI Biosciences, Inc., Boston, MA (US)

( * ) Notice: Subject to any disclaimer, the term of this patent is extended or adjusted under 35 U.S.C. 154(b) by 154 days.

(21) Appl. No.: 10/024,879

(22) Filed: Dec. 19, 2001

(65) Prior Publication Data

US 2002/0111676 A1 Aug. 15, 2002

Related U.S. Application Data (62) Division of application No. 09/420,527, filed on Oct. 19, 1999.
(60) Provisional application No. 60/251,215, filed on Dec. 4, 2000, and provisional application No. 60/105,031, filed on Oct. 20, 1998.

(51) Int. Cl.[7] .................................................. A61F 2/06
(52) U.S. Cl. ..................................... 623/2.41; 623/2.42
(58) Field of Search .............................. 623/2.41, 2.42, 623/3.1, 2.38, 2.39, 2.4, 2.15

(56) References Cited

U.S. PATENT DOCUMENTS

| | | | | |
|---|---|---|---|---|
| 4,687,483 A | * | 8/1987 | Fisher et al. | 623/2.14 |
| 5,770,193 A | | 6/1998 | Vacanti et al. | 424/93.7 |
| 5,984,973 A | * | 11/1999 | Girard et al. | 1/1 |

FOREIGN PATENT DOCUMENTS

WO     WO 97/41808     11/1997

OTHER PUBLICATIONS

Nathan, S., "Hearts valves may be grown," *Chemistry & Industry*, No. 9:330 (1995).

* cited by examiner

*Primary Examiner*—Corrine McDermott
*Assistant Examiner*—Hieu Phan
(74) *Attorney, Agent, or Firm*—Fish & Richardson P.C.

(57) ABSTRACT

Cardiovascular components such as biocompatible heart valves and annular sewing rings are disclosed, as well as, methods for making the same. The heart valves include biodegradable polymer fiber scaffolds and collagen. Also disclosed are donor aortic heart valves processed without the use of crosslinking chemicals.

6 Claims, 4 Drawing Sheets

Design of Mold for Casting a Semilunar Heart Valve

CARDIOVASCULAR COMPONENTS FOR TRANSPLANTATION AND METHODS OF MAKING THEREOF

PRIORITY DATA

This application is a divisional of U.S. application Ser. No. 08/420,527, filed on Oct. 19, 1999, which claims benefit to provisional applications 60/251,215, filed on Dec. 4, 2000 and 60/105,031, filed on Oct. 20, 1998.

BACKGROUND OF THE INVENTION

The heart includes four natural valves that function to regulate flow direction as blood is pumped between the lungs and the various blood vessels. The mitral and tricuspid valves, which are known as the atrioventricular or intraflow valves operate to prevent backflow into the atria during ventricular contraction while permitting blood to flow therethrough during ventricular relaxation. The aortic and pulmonary valves are known as semilunar or outflow valves and are located where blood leaves the heart.

Semilunar valves consist of three membranous cup-like structures or cusps attached, at the same level, to the wall of a cylindrical aortic vessel so that the cusps press on each other when they are filled with blood, preventing backflow in diastole. The direction of blood flow is upward. On contraction of the vessel, that is during systole, the cusps are pressed against the vessel wall by the force of blood flowing past the attached edges of the cusps toward the free edges of the cusps, allowing the blood to flow freely.

Each open pocket of the semilunar valve defines a volume called the aortic sinus which is filled with blood when the valve is closed. If the leaflet is cut away from the wall of the aorta it can be spread out in the form of a flat hemicircular membrane. The hemicircle is the edge of the leaflet which is attached to the wall of the aorta while the top more or less linear edge was the free edge of the leaflet. Each end of the leaflets called a commisure. The work of A. A. H. J. Sauren (The Mechanical behavior of the Aortic Valve (PhD thesis) Eindhoven, The Netherlands: Eindhoven Technical University, 1981), which is incorporated herein by reference, has shown in whole mounts of leaflets that the supporting scaffold of the leaflet consists of collagen fibers, having fractile properties, which extend from one commisure to the other providing support for the applied load of blood. Equations which describe the fiber system of the leaflet have been derived by C. S. Perkin and D. M. McQueen (Mechanical equilibrium determines the fractile fiber architecture of aortic heart valve leaflets. Am. J. Physiol. 266, H319-H328, 1994) from their function which is to support a uniform load when the aortic valve is closed. What they find is a single parameter family of collagen fibers with fractile properties which compare closely with the whole mount fiber preparations. Their work serves as the basis for creating a digital program which a textile machine, or a sewing machine, could use to reproduce an approximation of the fiber scaffold of the valve leaflet.

Histologically the leaflet consists of three tissue layers, the fibrosa, the spongiosa and the ventricularis. The fibrosa of the leaflet faces the aortic wall, enclosing the fiber system described above; the fiber scaffold is arranged in corrugated fashion permitting radial expansion of the valve leaflet. Adjacent to the fibrosa is the spongiosa, a loosely organized connective tissue with collagen elastin, proteoglycans and mucopolysaccharides. Furthest away from the aortic wall is the ventricularis consisting of a sheet of elastin thought to provide the tensile recoil needed to maintain the corrugated shape of the fibrosa. The surfaces of the leaflets in contact with the blood are covered by a layer of endothelial cells.

Heart valves, e.g., semilunar valves, are deformed by a variety of pathological processes. In many cases the diseased or defective valve can be surgically removed and replaced with a prosthetic valve. Two main types of artificial valves exist: (1) mechanical valves made from metal or plastic material; and (2) valves made from animal tissue.

Artificial valves, whether mechanical or made from animal tissue, have serious drawbacks. For example, mechanical valves carry a significant risk of thrombus formation. Also, the stress associated with the junction between the stent or frame and the biological portion of the bioprosthetic valve appears to be involved in structural failure over time. Valves made from animal tissue are typically crosslinked with chemicals, e.g., glutaraldehyde during processing. Treatment of the animal tissue with glutaraldehyde causes calcification and/or the structural breakdown of the tissue, thus, reducing the area available as binding sites for human host cells. In addition, both mechanical valves and valves constructed from animal tissue do not have the capacity to grow, i.e., these types of valves can neither be occupied or remodeled by host cells nor can they be biologically integrated.

A need exists, therefore, for an improved prosthetic heart valve that overcomes or minimizes the above-mentioned problems.

SUMMARY OF THE INVENTION

The invention features novel biocompatible cardiovascular components, e.g., semilunar heart valves, for transplantation. The invention also features methods for constructing these novel biocompatible cardiovascular components which preserve the nativity of the biological materials used. In addition, the invention features a novel annular sewing ring for attachment of a cardiovascular component to the aortic wall of a host. The components can be used in vitro, for example, for model systems for research, or in vivo as prostheses or implants to replace diseased or defective heart valves. In either case, the valves can be seeded with cells, e.g., spongiosa cells, fibrosa cells, ventricularis cells, smooth muscle cells, and/or endothelial and mesothelial cells.

In one aspect of the invention, the cardiovascular component is a semilunar valve which includes a biodegradable polymer fiber scaffold, e.g., a biopolymer fiber scaffold, and collagen. In a preferred embodiment, the collagen is fetal porcine collagen. In another preferred embodiment, the collagen is fibrillar collagen. In yet another preferred embodiment, the biopolymer fiber scaffold is a collagen biopolymer scaffold.

In another aspect of the invention, the cardiovascular component is a semilunar valve which includes a biodegradable polymer fiber scaffold, e.g., a biopolymer fiber scaffold, and collagen wherein the biopolymer scaffold fiber is derived from an aortic porcine valve processed in the absence of a crosslinking agent, e.g., glutaraldehyde.

In yet another aspect of the invention, the cardiovascular component is a semilunar valve which includes a biodegradable fiber scaffold, e.g., a biopolymer fiber scaffold, and collagen wherein the scaffold has a structure determined by a digital program.

The invention further pertains to a method of making a semilunar heart valve, comprising the steps of: (a) assembling a mold which replicates the structure of a semilunar heart valve having between two lateral edges a hollow representing the aortic root and hollows representing a plurality of leaflets with outer and inner surfaces, the inner surfaces connecting with the hollow representing the aortic root, thus, forming the intimal surface of the aortic root; (b) covering the intimal surface of the hollow representing the aortic root, i.e., the surface of the hollow representing the aortic root which connects, with the hollow representing the valve leaflets, and the outside surface of the hollow representing the valve leaflets, i.e., the surface away from the aortic wall with a biodegradable polymer fiber scaffold; (c) filling the hollow representing the aortic root and the hollows representing the plurality of leaflets with collagen, e.g., fetal porcine collagen, fibrillar collagen e.g., liquid dense fibrillar collagen; and (d) freeze-drying the polymer fiber scaffold and the liquid dense collagen forming a tissue with two lateral edges.

The invention still further pertains to an annular sewing ring for attachment of a heart valve to the aortic wall of a host which includes a biopolymer cloth and a biopolymer rope shaped in a circle, wherein the biopolymer cloth is wrapped around and stitched to the biopolymer rope.

The invention yet further pertains to a semilunar heart valve made according to a method which includes the steps of: (a) assembling a mold which replicates the structure of a semilunar heart valve having between two lateral edges a hollow representing the aortic root and hollows representing a plurality of leaflets with outer and inner surfaces, the inner surfaces connecting with the hollow representing the aortic root; (b) covering the intimal surface of the hollow representing the aortic root and the outside surface of the hollow representing the plurality of leaflets with a biodegradable polymer fiber scaffold; (c) filling the hollow representing the aortic root and the hollows representing the plurality of leaflets with liquid dense collagen; and (d) freeze-drying the polymer fiber scaffold and the liquid dense collagen forming a tissue with two lateral edges.

BRIEF DESCRIPTION OF THE DRAWINGS

FIG. 4A shows the back cover of the mold which represents the outside of the aorta.

FIG. 4B shows the front cover of the mold which represents the inside of the aorta displaying the attached leaflet molds.

FIG. 4C shows the back side of the front cover of the mold displaying the back side of the leaflet molds as they join with the aorta.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention features novel biocompatible cardiovascular components for transplantation, e.g., heart valves, e.g., semilunar heart valves. The term "biocompatible" as that term is used herein, means exhibition of essentially no cytotoxicity while in contact with body fluids or tissues. "Biocompatibility" also includes essentially only minimal interactions, i.e., interactions leading to immune rejection or to persistent inflammation responses, with recognition proteins, e.g., naturally occurring antibodies, cell proteins, cells, and other components of biological systems. The invention also features methods of making these components which preserves the nativity of the biological material comprising the components.

In one aspect of the invention, the cardiovascular component is a heart valve, e.g., a semilunar heart valve which includes a biodegradable polymer fiber scaffold, e.g., a biopolymer fiber scaffold, and collagen. A semilunar heart valve is composed of three membranous cup-like structures or cusps attached, at the same level, to the wall of a cylindrical arterial vessel, e.g., the aorta, so that the cusps press on each other when they are filled with blood, preventing backflow in diastole. Methods for making the polymer fibers which comprise the polymer fiber scaffolds are taught in U.S. Pat. No. 5,851,290, entitled "Apparatus and Method for Spinning and Processing Collagen Fiber," which is incorporated herein by reference.

The term "biodegradable polymers," as that term is used herein, includes any polymer that naturally degrades or breaks down over time by hydrolysis, for example, poly-α-hydroxyesters such as poly-1-lactic acid and poly-1-glycolic acid, polydioxinone, polyvinyl alcohol, surgical gut, and combinations thereof, or which degrades over time by enzymatic action, for example, biopolymer, e.g., collagen.

A biopolymer is a naturally occurring polymeric substance formed from individual molecules in a biological system or organism. Biopolymers can also be man-made by manipulation of the individual molecules once obtained outside the biological system or organism. The biopolymer is suitable for introduction into a living organism, e.g., a mammal, e.g., a human. The biopolymer is non-toxic and bioabsorbable when introduced into a living organism and any degradation products of the biopolymer should also be non-toxic to the organism. The biopolymers of the invention can be formed into cardiovascular components, e.g., heart valves, e.g., semilunar heart valves, which include biocompatible fibers, e.g., collagen fibers, biocompatible fabrics, e.g., collagen fabrics. Examples of molecules which can form biopolymers and which can be used in the present invention include collagen, laminin, elastin, fibronectin, fibrinogen, thrombospondin, gelatin, polysaccharides, polylamino acids and combinations thereof. In one embodiment, a combination or mixture of one or more biopolymers can be used to form the cardiovascular components, e.g., heart valves, e.g., semilunar heart valves, of the invention. For example, a combination of laminin and type IV collagen can be used to form the biopolymer fibers described herein. A preferred molecule for biopolymer production is collagen.

Preferred sources of molecules which form biopolymers include mammals such as pigs, e.g., near-term fetal pigs, sheep, fetal sheep, cows, and fetal cows. Other sources of the molecules which can form biopolymers include both land and marine vertebrates and invertebrates. In one embodiment, the collagen can be obtained from skins of near-term, domestic porcine fetuses which are harvested intact, enclosed in their amniotic membranes. Collagen or combinations of collagen types can be used in the cardiovascular components, e.g., heart valves, e.g., semilunar heart valves described herein. A preferred type of collagen is porcine fetal collagen. Another preferred type of collagen is fibrillar collagen, e.g., fibrillar collagen can be produced by processing a solution of monomeric liquid collagen, e.g., non-polymeric liquid collagen. Fibrillar collagen is a type of collagen which contains fibrils. The language "fibrillar collagen" or "collagen microfibril" is art recognized and is intended to include collagen in the form described in Williams, B. R. et al. (1978) *J. Biol. Chem.* 253 (18):6578-6585 and U.S. patent application Ser. No. 08/910,853, filed Aug. 13, 1997, entitled "Compositions, Devices, and Methods for Coagulating Blood" by Eugene Bell and Tracy M. Sioussat, the contents of which are incorporated herein by reference. In a preferred embodiment, the collagen microfibrils are prepared according to the methods taught in U.S. Patent Application Ser. No. 60/095,627, entitled "Bone Precursor Compositions," which are incorporated herein by reference. Liquid dense fibrillar collagen is fibrillar collagen in a liquid form which can be dried to a dense fibrillar tissue, e.g, a matt. Biopolymer and collagen matts are described in copending patent application Ser. No. 09/042,549, entitled "Biopolymer Matt for Use in Tissue Repair and Reconstruction," the contents of which are incorporated herein by reference.

Examples of collagen or combinations of collagen types include collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, and collagen type XVII. A preferred combination of collagen types includes collagen type I, collagen type III, and collagen type IV.

Preferred mammalian tissues from which to extract the molecules which can form biopolymer include entire mammalian fetuses, e.g., porcine fetuses, dermis, tendon, muscle and connective tissue. As a source of collagen, fetal tissues are advantageous because the collagen in the fetal tissues is not as heavily crosslinked as in adult tissues. Thus, when the collagen is extracted using acid extraction, a greater percentage of intact collagen molecules is obtained from fetal tissues in comparison to adult tissues. Fetal tissues also include various molecular factors which are present in normal tissue at different stages of animal development.

In a preferred embodiment, the cardiovascular components, e.g., heart valves, e.g., semilunar heart valves, are collagen cardiovascular components, e.g., collagen heart valves, e.g., collagen semilunar heart valves. Collagen solutions can be produced by salt extraction, acid extraction, and/or pepsin extraction from the starting material. In a preferred embodiment, the collagen used is produced by sequentially purifying two forms of collagen from the same collagen-containing starting material. First, intact collagen is acid extracted from the starting material, the extract is collected and collagen is prepared as a collagen solution, e.g., by precipitating the collagen with sodium chloride and solubilizing the collagen in a medium having an acidic pH. Meanwhile, truncated collagen, i.e., collagen from which the teleopeptides have been cleaved or partly cleaved leaving only the helical portion or the helical portion with some telopeptides, is extracted from the starting material using enzyme, e.g., an enzyme which is functional at an acidic pH, e.g., pepsin, extraction. Then, the collagen from this pepsin extract is purified separately by similar methods as from the first extract.

Proteins necessary for cell growth, morphogenesis, differentiation, and tissue building can also be added to the biopolymer molecules or to the biopolymer fibrils to further promote cell ingrowth and tissue development and organization within the cardiovascular components, e.g., hearts valves, e.g., semilunar heart valves. The phrase "proteins necessary for cell growth, morphogenesis, differentiation, and tissue building" refers to those molecules, e.g., proteins which participate in the development of tissue. Such molecules contain biological, physiological, positional, and structural information for development or regeneration of the tissue structure and function. Examples of these macromolecules include, but are not limited to, sonic hedgehog; NK-2, XNKx-3.3 (tinman), hCsx and Gax homeobox gene products; TGFbeta, VEGF, FGF, IGF, PDGF, BMP4 cytokine proteins, growth factors, extracellular matrix proteins, proteoglycans, glycosaminoglycans and polysaccharides. Alternatively, the cardiovascular components, e.g., heart valves, e.g., semilunar heart valves of the invention can include extracellular matrix macromolecules in particulate form or extracellular matrix molecules deposited by cells or viable cells or deliberately added to the valve scaffold. Methods for processing tissues for making extracellular matrix macromolecules in particulate form are taught in U.S. Pat. No. 5,800,537, entitled "A Method and Construct for Producing Graft Tissue From Extracellular Matrix," the contents of which are incorporated herein by reference.

The collagen used to create the cardiovascular components, e.g., heart valves, e.g., semilunar heart valves, may be enriched with signaling molecules which play a role in vascular development. Products of three classes of genes are implicated: hedgehog, homeobox and cytokine. They include but are not limited to the following proteins: sonic hedgehog; NK-2, XNKx-3.3 (tinman), hCsx and Gax homeobox gene products; TGFbeta, VEGF, FGF, IGF, PDGF, and BMP4 cytokine proteins. Differentiation induced by the use of combinations of the foregoing proteins is promoted by incubation of the cell laden scaffold in vitro under tissue culture conditions.

The term "growth factors" is art recognized and is intended to include, but is not limited to, one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-β1, TGF-β1.2, TGF-β2, TGF-β3, TGF-β5; vascular endothelial growth factors (VEGF), e.g., VEGE, epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M, BMP cytokine proteins; nerve growth factor (NGF); stem cell factor; hepatocyte growth factor, and ciliary neurotrophic factor. The term encompasses presently unknown growth factors that may be discovered in the future, since their characterization as a growth factor will be readily determinable by persons skilled in the art.

The term "extracellular matrix proteins" is art recognized and is intended to include one or more of fibronectin, laminin, vitronectin, tenascin, entactin, thrombospondin, elastin, gelatin, collagens, fibrillin, merosin, anchorin, chondronectin, link protein, bone sialoprotein, epinectin, hyaluronectin, undulin, epiligrin, and kalinin. The term encompasses presently unknown extracellular matrix proteins that may be discovered in the future, since their characterization as an extracellular matrix protein will be readily determinable by persons skilled in the art.

The term "proteoglycan" is art recognized and is intended to include one or more of decorin and dermatan sulfate proteoglycans, keratin or keratan sulfate proteoglycans, aggrecan or chondroitin sulfate proteoglycans, heparan sulfate proteoglycans, biglycan, syndecan, perlecan, or serglycin. The term encompasses presently unknown proteoglycans that may be discovered in the future, since their characterization as a proteoglycan will be readily determinable by persons skilled in the art.

The term "glycosaminoglycan" is art recognized and is intended to include one or more of heparan sulfate, chondroitin sulfate, dermatan sulfate, keratan sulfate, hyaluronic acid. The term encompasses presently unknown glycosaminoglycans that may be discovered in the future, since their characterization as a glycosaminoglycan will be readily determinable by persons skilled in the art.

The term "polysaccharide" is art recognized and is intended to include one or more of heparin, dextran sulfate, chitin, alginic acid, pectin, and xylan. The term encompasses presently unknown polysaccharides that may be discovered in the future, since their characterization as a polysaccharide will be readily determinable by persons skilled in the art.

Suitable living cells include, but are not limited to, cells derived from the layers of tissue comprising the semilunar heart valve, e.g., spongiosa, fibrosa, and ventricularis cells, epithelial cells, and mesothelial cells, e.g., keratinocytes, adipocytes, hepatocytes, neurons, glial cells, astrocytes, podocytes, mammary epithelial cells, islet cells; endothelial cells, e.g., aortic, capillary and vein endothelial cells; and mesenchymal cells, e.g., dermal fibroblasts, mesothelial cells, stem cells, osteoblasts, smooth muscle cells, striated muscle cells, ligament fibroblasts, tendon fibroblasts, chondrocytes, and fibroblasts.

In one embodiment, when the biopolymer is collagen, the collagen can be treated with an enzyme, e.g., lysyl oxidase which primes the collagen for crosslinking. Lysyl oxidase, which can be purified from a variety of sources including, for example, calf aorta, human placenta, chicken embryo epiphyseal cartilage, pig skin, (see Shackleton, D. R. and Hulmes, D. J. S. (1990) *Biochem. J.* 266:917-919), and several locations in pig embryos, converts the E-amino group of lysine to an aldehyde. This aldehyde is a reactive functional group which spontaneously binds to other lysine ε-amino groups or other aldehydes on other collagen molecules to form irreversible covalent crosslinks. The result is that collagen becomes insoluble. Lysyl oxidase can be added to the collagen solutions under conditions which allow for the aldehyde conversion of the lysines. The lysyl oxidase is then removed from the collagen solution and the collagen is processed as described herein during which the spontaneous crosslinks form. For example, during the processing of the collagen cardiovascular component, e.g., during the polymerization step, the crosslinks spontaneously form as the concentration of collagen per unit volume increases. The lysyl-oxidase-mediated crosslink is strong, irreversible and is a linkage naturally found in collagen. Collagen crosslinked in this manner is insoluble and susceptible only to specific enzymatic attack during remodeling of tissues. Lysyl oxidase can also be used to crosslink collagen for use as matt and matt compositions as well as spun fibers, gels, etc.

In still another embodiment, the strength of the cardiovascular component can be increased by standard collagen crosslinking methods using, e.g., ultraviolet, dehydrothermal, or chemical crosslinkers. Typical chemical crosslinkers include, for example, glutaraldehyde, formaldehyde, acrylamide, carbodiimides, such as those known in the art, e.g., 1-ethyl-3-(dimethyaminopropyl) carbodiimide, diones known to those skilled in the art, e.g., 2,5-hexanedione, diimidates, e.g., dimethylsuberimidate, or bisacrylamides, e.g., N,N'-methylenebisacrylamide.

In still yet another embodiment of the invention, the cardiovascular components, e.g., heart valves, e.g., semilunar heart valves, comprise biopolymer fiber scaffold derived from an aortic porcine valve processed in the absence of a crosslinking agent, e.g., glutaraldehyde or chemicals similar thereto. By eliminating the step of treating an aortic porcine valve with glutaraldehyde or with chemicals similar to glutaraldehyde, the calcification or structural breakdown of the aortic porcine valve tissue is eliminated. Accordingly, binding sites for host human cells and other cells are maintained with the present invention.

Moreover another embodiment of the invention, the cardiovascular components, e.g., heart valve, e.g., semilunar heart valve, comprise a biodegradable polymer fiber scaffold, e.g., a biopolymer fiber scaffold, having a structure determined by a digital program. The work of A. A. H. J. Sauren (The Mechanical behavior of the Aortic Valve (PhD thesis) Eindhoven, The Netherlands: Eindhoven Technical University, 1981), which is incorporated herein by reference, has shown in whole mounts of leaflets that the supporting scaffold of the leaflet consists of collagen fibers, having fractile properties, which extend from one commissure to the other providing support for the applied load of blood. Equations which describe the fiber system of the leaflet have been derived by C. S. Perkin and D. M. McQueen (Mechanical equilibrium determines the fractile fiber architecture of aortic heart valve leaflets. *Am. J. Physiol.* 266, H319-H328, 1994) from their function which is to support a uniform load when the aortic valve is closed. What they found is a single parameter family of collagen fibers with fractile properties which compare closely with the whole mount fiber preparations. Their work serves as the basis for creating a digital program which a textile machine, or a sewing machine, could use to reproduce an approximation of the fiber scaffold of the valve leaflet.

The present invention also features a novel biocompatible annular sewing ring for attachment of a heart valve to the aortic wall of a host. The annular ring is comprised of a biopolymer, e.g., collagen. In a preferred embodiment, the biopolymer, e.g., collagen, is a biopolymer fiber, e.g., collagen fiber.

Figure 1:
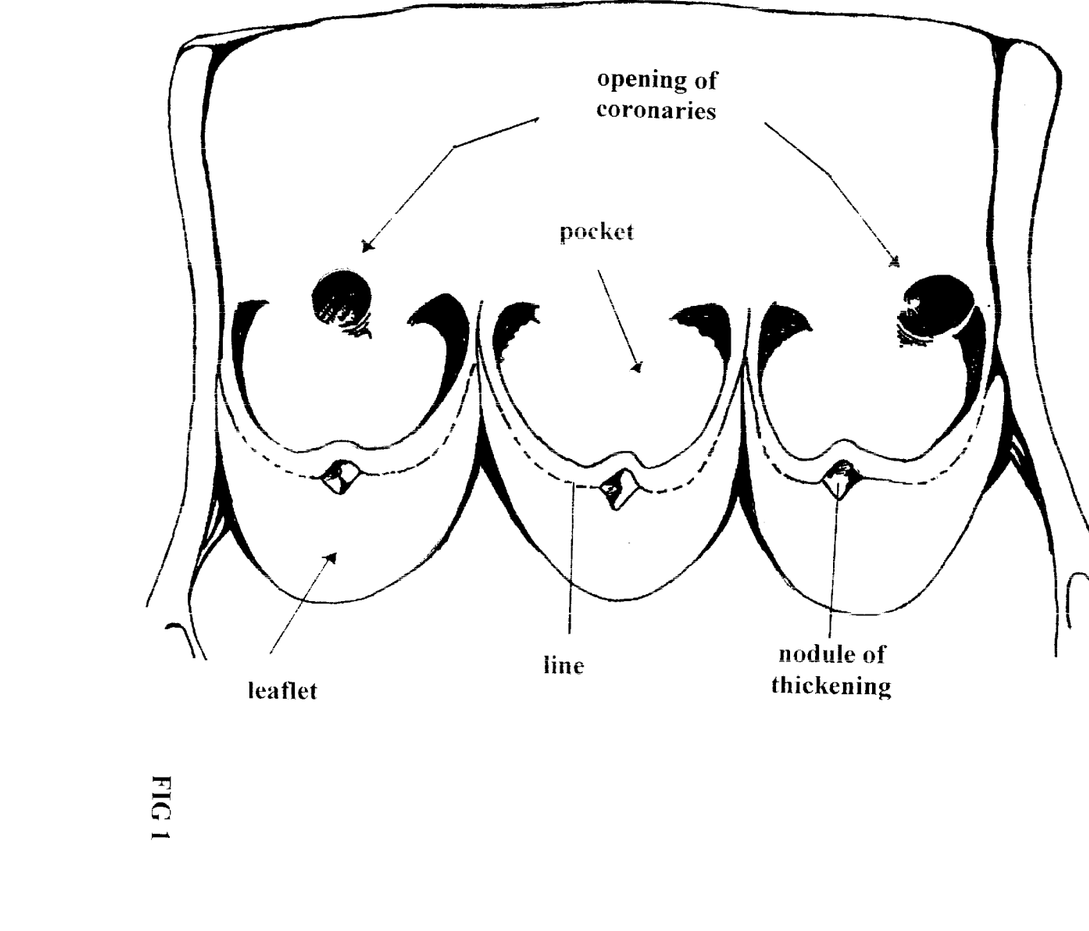
FIG. 1 shows the aorta slit open longitudinally and laid flat so that the structure of the valve leaflets of the semilunar valve can be displayed.
Figure 2:
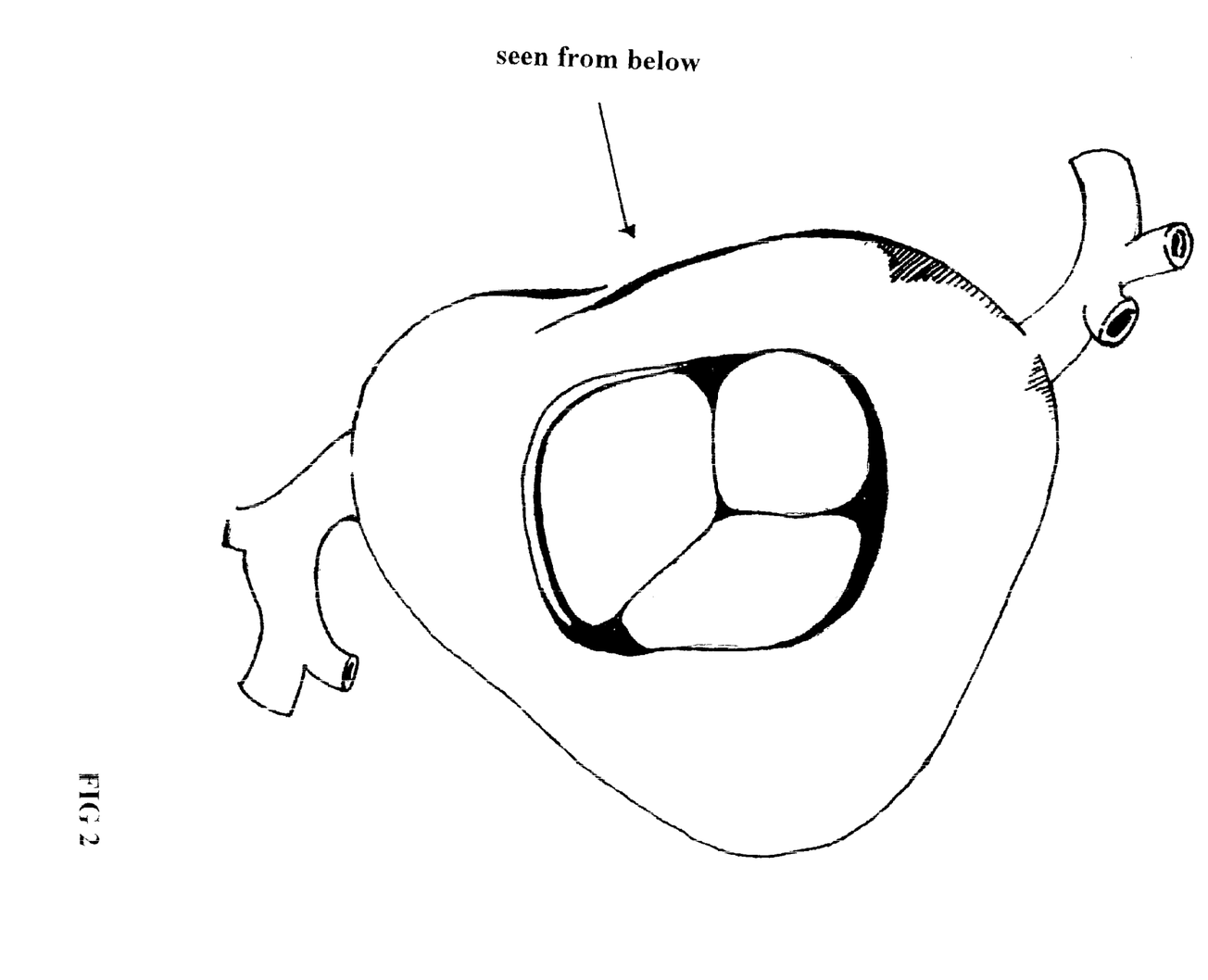
FIG. 2 shows the valve leaflets of the semilunar valve from below in the closed condition; filled with blood and pressing on each other thereby preventing backflow.
Figure 4:
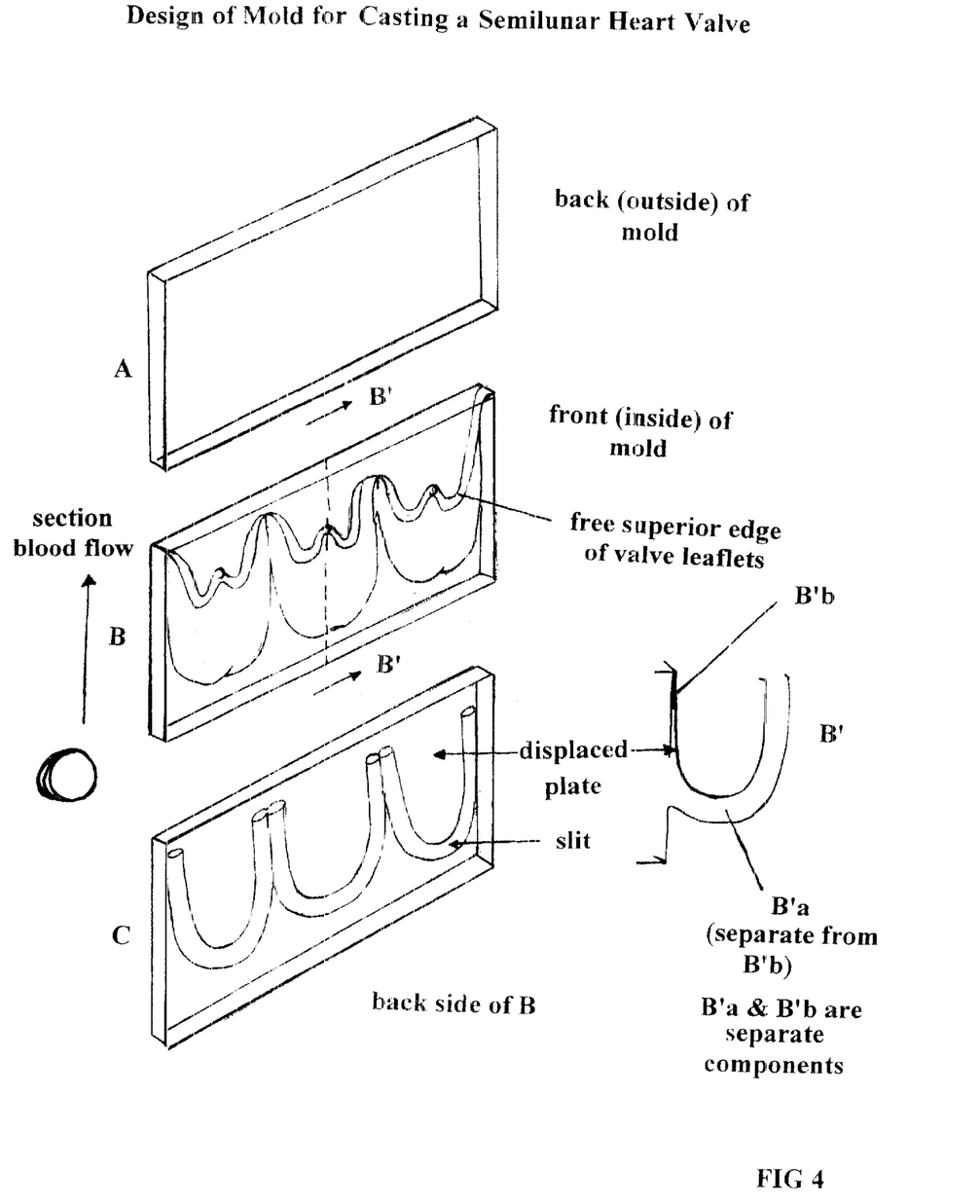
FIG. 4 shows the mold design for constructing a semilunar heart valve.

Referring to the figures, the semilunar valve of the aorta consists of three leaflets or cusps which resemble pockets attached to the wall of the aorta along their inferior edge (FIG. 1) with the superior edge of each pocket being free. If the wall of the aorta is slit between two leaflets along a vertical axis and the aorta is opened, three leaflets resembling pockets, all in a row, are seen attached to the flattened aortic wall or root. The aorta or the aortic root and its attached leaflets can be made in a mold; for example, a mold consisting of three parts which fit together tightly to make a closed aortic wall to which the three pocket like structures are attached (FIG. 4).

The parts of the mold for replicating a semilunar heart valve can be constructed from inert materials, e.g., stainless steel or stainless steel coated with Teflon®. An example of such a mold is shown in FIG. 4. Referring to FIG. 4, the mold includes three integral parts, which are shown in views A, B, and C. The three parts fit together between two lateral edges to form a box with a hollow interior to form the aortic root and attach to three valve leaflets by interconnecting U-shaped channels. The first part (A) is shaped as a rectangular box cover which represents the back or outside wall of the aorta, e.g., the aortic root. The second part (B) also employs a rectangular shape and fits together with the first part A to form the front or inside wall of the aorta. The second part (B) itself includes a front and back side which represent the front or inside walls and the back or outside walls, respectively, of the valve leaflets or cusps which attach to the front or inside wall of the aorta (A). The front or inside walls of the valve leaflets are represented on the front side of the second part (B) as hollow pockets which include the free edge, the nodulus arantis, the commisures, and the lower edge of each valve leaflet. The commisures and the lower edge of each valve leaflet, which form the hollow pockets, communicate with the aorta and are represented by hollow U-shaped channels which penetrate the wall of the second part (B and C). The third part includes a plate (C) which forms the outside face of each valve leaflet, i.e., the face intimal with the aorta. The third part completes the hollow channels which form the valve leaflets (B'a and B'b) and includes a U-shaped curve structure that attaches to the back of the second part. The bottom of the U-shaped curve of the third part (B'a) includes a wider diameter than the other areas of the communicating hollows (B', C) to form the base or floor of the bottom edge of each valve leaflet.

With an assembled mold, sheets of a biodegradable polymer fiber scaffold, e.g., a biopolymer fiber scaffold, e.g., a collagen fiber scaffold, e.g., a woven (braided, knitted) collagen fiber scaffold, are laid into the respective hollows (B) of the mold so that they lie in contact with the intimal surface of the aortic root and with the outside surface of the valve pockets, i.e., the surface away from the aortic wall. The sheets of a biodegradable polymer fiber scaffold, e.g., a biopolymer fiber scaffold, e.g., a collagen fiber scaffold, e.g., a woven (braided, knitted) collagen fiber scaffold, extend into the U shaped slit and are bent to overlap the displaced plate (C) so that they lie in contact with the intimal surface of the aortic wall. Fiber scaffolds containing more than one type of biodegradable polymers can also be formed, for example, by combining a biodegradable polymer fiber scaffold with a collagen fiber scaffold in the hollows of the mold as described above.

Figure 3:
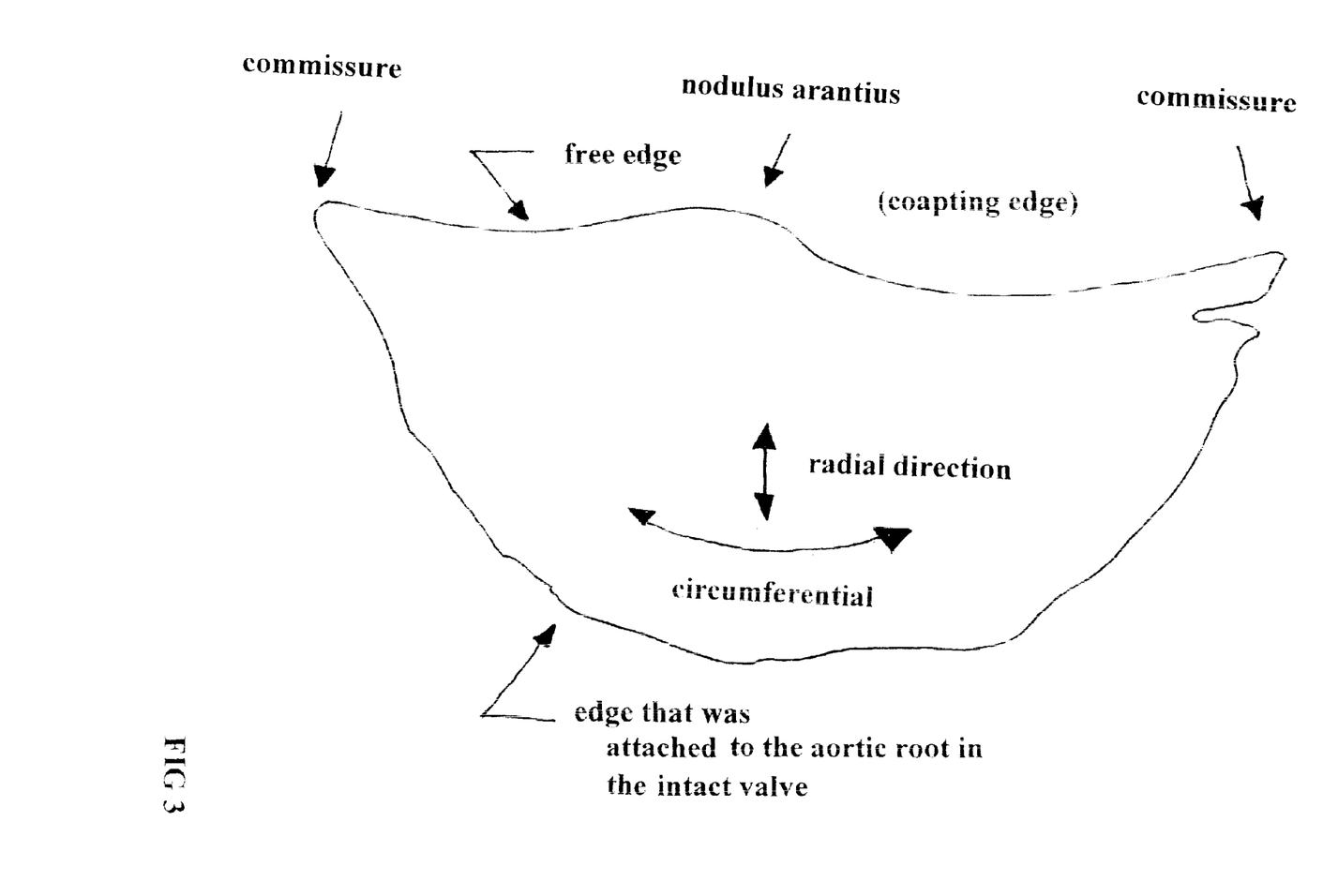
FIG. 3 shows the valve leaflets of the semilunar valve schematically in longitudinal section.

In a preferred embodiment, a crosslinked collagen fiber scaffold is laid into the respective hollows of the mold. In another preferred embodiment, a biopolymer fiber scaffold comprised of processed pig heart valves can be laid into the respective hollows of the mold. In yet another preferred embodiment, sheets of woven collagen threads constructed from a textile machine can be laid into the respective hollows of the mold. As described previously, from equations for the collagen fiber support system for the valve leaflet or cusp, a digital program can be written for a textile or sewing machine which can produce a collagen fiber scaffold in the form of three cusps using the crosslinked collagen fibers described immediately above. Even without such a program from information already available the general pattern of the fiber system can be reproduced. For example each cusp can have the geometry of the expanded cusp shown in FIG. 3, but cusps would be connected at the commisures.

The hollows of the mold are then filled with collagen, e.g., fetal porcine, fibrillar collagen, e.g., liquid dense fibrillar collagen. In a preferred embodiment, the third part of the mold (C, B'b) is removed and the fiber reinforced collagen which has formed lining the aortic wall and the valve leaflet is seeded with cells which would normally populate the respective tissues of the semilunar valve, e.g., cells derived from the fibrosa, spongiosa, and ventricularis tissues. The mold can then be introduced into a cell culturing system to allow attachment, growth, and differentiation of the seeded cells. In another preferred embodiment, the valve is seeded with cells which normally populate the outer tissue covering the semilunar valve, e.g., allogeneic or autogenous endothelial or mesothelial cells, to provide an epithelial covering to the valves and aorta. These endothelial or mesothelial cells are used to populate all tissue surfaces except the back or outer surface of the aortic wall after the first cells seeded into the tissue have remodeled the biopolymer structure.

As described supra, the collagen, e.g., fetal porcine collagen, e.g., liquid dense fetal porcine collagen, used to fill the components of the mold may be enriched with signaling molecules which play a role in vascular development.

Cardiovascular complexes of signaling molecules can be derived from the extracellular matrix of young or very young porcine fetuses containing the proteins listed below. Products of three classes of genes are implicated: hedgehog, homeobox and cytokine. They include but are not limited to the following proteins: sonic hedgehog; NK-2, XNKx-3.3 (tinman), hCsx and Gax homeobox gene products;

TGFbeta, VEGF, FGF, IGF, PDGF, and BMP4 cytokine proteins. Differentiation induced by the use of combinations of the foregoing proteins is promoted by incubation of the cell laden scaffold in vitro under tissue culture conditions.

The tissue which has formed can be lifted out of the mold and the two lateral edges of the valve are sewn together with a biopolymer thread, e.g., collagen or synthetic thread, to form a tubular valve. In a preferred embodiment, additional endothelial or mesothelial cells may be seeded onto the structure to cover the intimal surface of the aorta and the surfaces of the valve leaflets. In another embodiment, the tubular valve can be incorporated into a pulsatile closed circulatory loop containing a nutrient fluid having the viscoelastic properties of blood. The valve can be oriented in the circulation so that during diastole it back flows to fill the pockets of the valve. Mechanical conditioning of the valve can be carried out for a period of 2–4 weeks. It can remain in culture ready for delivery on demand.

As described supra, the heart valves, e.g., semilunar valves, of animals, e.g., the pig heart, have been used as substitutes for defective human valves for many years. The usual procedure for processing the valves after removal from an animal consists of crosslinking them with chemicals, e.g., glutaraldehyde. Chemicals such as glutaraldehyde destroy all biological information associated with the scaffold of the valve. Accordingly, chemicals such as glutaraldehyde cause the tissue of the removed valve to calcify and/or breakdown structurally, thus, eliminating binding sites for cells, e.g., human host cells, which might otherwise be expected to seed into the leaflets of the valves as well as into the cuffs of the valves. There is also the loss of binding sites that would otherwise permit endothelial or mesothelial cells to populate the surfaces of the valve structures. To overcome these limitations the following method has been developed to process the valves after removal from the donor animal. This method eliminates the chemical crosslinking step, e.g., crosslinking with glutaraldehyde.

In a preferred embodiment, the valve, e.g., the semilunar valve, is removed from the donor animal, e.g., a pig. Using a 10% solution of NAOH, cellular components are stripped from the collagen fiber scaffold of the valve leaflets and annulus (the aortic wall), thus, eliminating viruses, and other microorganisms, cells and cell surface antigenic determinants retaining the fibrous scaffold. The processed valve can then be laid into a valve mold, e.g., the semilunar mold described supra, and be formed into a heart valve for transplantation.

In a preferred embodiment, the processed donor valve is laid into the respective hollows (B) of the mold so that they lie in contact with the intimal surface of the aortic root and with the outside surface of the valve pockets, i.e., the surface away from the aortic wall. The donor valve, e.g., pig valve, e.g., the pig semilunar valve, extend into the U shaped slit and are bent to overlap the displaced plate (C) so that they lie in contact with the intimal surface of the aortic wall. The hollows of the mold are then filled with collagen, e.g., fetal porcine collagen, or fibrillar collagen e.g., liquid dense fibrillar collagen. In a preferred embodiment, the contents of the mold are freeze dried to form a structure, e.g., a biopolymer foam, e.g., a collagen foam around the donor valve. Methods for freeze drying collagen and forming biopolymer foams and collagen foams of varying densities are taught in U.S. Pat. Nos. 5,891,558 and 5,709,934, each entitled "Biopolymer Foams for Use in Tissue Repair and Reconstruction," the contents of which are incorporated herein by reference.

In a preferred embodiment, as described supra, the third part of the mold (C, B'b) is removed and the donor valve reinforced foam which has formed lining the aortic wall and the valve leaflet is seeded with cells which would normally populate the respective tissues of the semilunar valve, e.g., cells derived from the fibrosa, spongiosa, and ventricularis tissues. The mold can then be introduced into a cell culturing system to allow attachment, growth, and differentiation of the seeded cells. In another preferred embodiment, the valve is seeded with cells which normally populate the outer tissue covering the semilunar valve, e.g., allogeneic or autogenous endothelial or mesothelial cells, to provide an epithelial covering to the valves and aorta. These endothelial or mesothelial cells are used to populate all tissue surfaces except the back or outer surface of the aortic wall after the first cells seeded into the tissue have remodeled the biopolymer structure.

As described supra, the collagen, e.g., fetal porcine collagen, or fibrillar collagen, e.g., liquid dense fibrillar collagen, used to fill the components of the mold may be enriched with signaling molecules which play a role in vascular development. Products of three classes of genes are implicated: hedgehog, homeobox and cytokine. They include but are not limited to the following proteins: sonic hedgehog; NK-2, XNKx-3.3 (tinman), hCsx and Gax homeobox gene products; TGFbeta, VEGF, FGF, IGF, PDGF, and BMP4 cytokine proteins. Differentiation induced by the use of combinations of the foregoing proteins is promoted by incubation of the cell laden scaffold in vitro under tissue culture conditions.

The tissue which has formed can be lifted out of the mold and the two lateral edges of the valve are sewn together with a biopolymer thread, e.g., collagen or synthetic thread, to form a tubular valve.

In a preferred embodiment, the valve is rehydrated in tissue culture medium and seeded with fibroblasts internally and with endothelial cells on its surfaces to demonstrate cell attachment, absence of toxicity, cell proliferation and differentiation. The toxicity and low information content of glutaraldehyde treated tissues which prevent the repopulation of processed valves are no longer a problem when valves are prepared by the methods of this disclosure.

In another embodiment, the tubular valve can be incorporated into a pulsatile closed circulatory loop containing a nutrient fluid having the visco-elastic properties of blood. The valve can be oriented in the circulation so that during diastole it back flows to fill the pockets of the valve. Mechanical conditioning of the valve can be carried out for a period of 2–4 weeks or longer. It can remain in culture ready for delivery on demand.

The invention also features a biocompatible annular sewing ring which can be used for attachment of a valve, e.g., a heart valve, e.g., a semilunar valve, to the aorta. In one embodiment, a biopolymer cloth or biopolymer matt, e.g., a collagen cloth or collagen matt, is prepared. Biopolymer and collagen matts are described in copending patent application Ser. No. 09/042,549, entitled "Biopolymer Matt for Use in Tissue Repair and Reconstruction," the contents of which are incorporated herein by reference. The biopolymer cloth or matt, e.g., collagen cloth or matt, can be wrapped around and stitched to a biopolymer matt in a rope-like structure, e.g., a collagen matt rope shaped as a circle and stitched to the rope. Various shaped biopolymer matts, e.g., various shaped collagen matts, are described in copending patent application Ser. No. 09/042,549, entitled "Biopolymer Matt for Use in Tissue Repair and Reconstruction," the contents of which are incorporated herein by reference. These, biopolymer matts, e.g., collagen marts, can be cast into various shapes, e.g., tubes or orbs, such as spheres, to produce membranous structures which can contain material or liquids for specialized functions. Examples of implants made from matt, matt composite, or matt compositions include, for example, vessels, ducts, ureters, bladders and bone implants. Biopolymer marts, e.g., collagen matts, can be cast as tubes or orbs, such as spheres, to produce membranous structures which can contain material or liquids for specialized functions. Examples of implants made from matt, matt composite, or matt compositions include, for example, vessels, ducts, ureters, bladders and bone implants from matt cylinders filled with bone replacement material.

In a preferred embodiment, the biocompatible annulus, e.g., the collagen annulus, can be seeded with cells and enriched with signaling molecules which play a role in vascular development. Products of three classes of genes are implicated: hedgehog, homeobox and cytokine. They include but are not limited to the following proteins: sonic hedgehog; NK-2, XNKx-3.3 (tinman), hCsx and Gax homeobox gene products; TGFbeta, VEGF, FGF, IGF, PDGF, and BMP4 cytokine proteins. Differentiation induced by the use of combinations of the foregoing proteins is promoted by incubation of the cell laden scaffold in vitro under tissue culture conditions. In another preferred embodiment, additional endothelial or mesothelial cells may be seeded onto the structure to cover the outer surface of the biocompatible annulus.

The contents of all cited references including literature references, issued patents, published patent applications, and co-pending patent applications cited throughout this application including the background are hereby expressly incorporated by reference in their entirety.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. An annular sewing ring for attachment of a heart valve to the aortic wall of a host, comprising:
   a biopolymer cloth and a biopolymer rope shaped in a circle, wherein the biopolymer cloth is wrapped around and stitched to the biopolymer rope.

2. The annular sewing ring of claim 1, wherein the biopolymer fiber cloth is collagen cloth and the biopolymer rope is collagen rope.

3. The annular sewing ring of claim 2, wherein the collagen is selected from the group consisting of collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, and collagen type XVII.

4. The annular sewing ring of claim 1, wherein the ring is seeded with cells which normally populate semilunar valve tissue.

5. The annular sewing ring of claim 1, wherein the ring is enriched with signaling molecules.

6. The annular sewing ring of claim 1, wherein the signaling molecules are selected from the group consisting of sonic hedgehog; NK-2, XNKx-3.3 (tinman), hCsx and Gax homeobox gene products; TGFbeta, VEGF, FGF, IGF, PDGF, and BMP4 cytokine proteins.

* * * * *